United States Patent
Sturgess et al.

(10) Patent No.: US 7,498,307 B2
(45) Date of Patent: Mar. 3, 2009

(54) COMBINATIONS OF DNAK INHIBITORS WITH KNOWN ANTIBACTERIAL AGENTS

(76) Inventors: Michael Alan Sturgess, 2193 Esten Rd., Quakertown, PA (US) 18951; Kenneth E. Kovan, 2 Evergreen Ave., Wayne, PA (US) 19087

(*) Notice: Subject to any disclaimer, the term of this patent is extended or adjusted under 35 U.S.C. 154(b) by 242 days.

(21) Appl. No.: 11/155,409

(22) Filed: Jun. 17, 2005

(65) Prior Publication Data

US 2006/0287238 A1    Dec. 21, 2006

(51) Int. Cl.
*A61K 38/16*    (2006.01)
(52) U.S. Cl. .......................................... 514/12; 530/324
(58) Field of Classification Search ................... 514/12; 530/324

See application file for complete search history.

(56) References Cited

U.S. PATENT DOCUMENTS

| | | | | |
|---|---|---|---|---|
| 4,382,892 A | * | 5/1983 | Hayakawa et al. | 540/575 |
| 6,605,295 B1 | * | 8/2003 | Bellmann et al. | 424/427 |
| 6,667,057 B2 | * | 12/2003 | Rudnic et al. | 424/468 |
| 7,015,309 B1 | * | 3/2006 | Otvos | 530/350 |

* cited by examiner

*Primary Examiner*—David Lukton
(74) *Attorney, Agent, or Firm*—Fox Rothschild LLP; Gerard P. Norton; Shahnam Sharareh

(57) ABSTRACT

Compositions, methods and kits are provided comprising (a) a therapeutically effective amount of a DnaK inhibitor; and (b) a therapeutically effective amount of a known antibacterial agent. Such compositions, methods and kits are useful in the treatment of various bacterial infections.

18 Claims, 6 Drawing Sheets

SEQUENCE LISTING

<160> NUMBER OF SEQ ID NOS: 5

<210> SEQ ID NO 1
<211> LENGTH: 18
<212> TYPE: PRT
<213> ORGANISM: Pyrrhocoris
<220> FEATURE:
<221> NAME/KEY: MOD_RES
<222> LOCATION: (18)..(18)
<223> OTHER INFORMATION: Residue is optionally modified with a C1-C6 alkyl

<400> SEQUENCE: 1

Asp Leu Gly Ser Tyr Leu Pro Arg Pro Thr Pro Pro Arg Pro Ile Tyr
1               5                   10                  15

Asn Arg

<210> SEQ ID NO 2
<211> LENGTH: 5
<212> TYPE: PRT
<213> ORGANISM: Pyrrhocoris

<400> SEQUENCE: 2

Lys Val Asp Lys Val
1               5

<210> SEQ ID NO 3
<211> LENGTH: 10
<212> TYPE: PRT
<213> ORGANISM: Pyrrhocoris

<400> SEQUENCE: 3

Arg Pro Pro Thr Pro Arg Pro Leu Lys Val
1               5                   10

<210> SEQ ID NO 4
<211> LENGTH: 20
<212> TYPE: PRT
<213> ORGANISM: Pyrrhocoris

<400> SEQUENCE: 4

Val Asp Lys Gly Ser Tyr Leu Pro Arg Pro Thr Pro Pro Arg Pro Ile
1               5                   10                  15

Tyr Asn Arg Asn
            20

<210> SEQ ID NO 5
<211> LENGTH: 19
<212> TYPE: PRT
<213> ORGANISM: Drosophila

<400> SEQUENCE: 5

Gly Lys Pro Arg Pro Tyr Ser Pro Arg Pro Thr Ser His Pro Arg Pro
1               5                   10                  15

Ile Arg Val

COMBINATIONS OF DNAK INHIBITORS WITH KNOWN ANTIBACTERIAL AGENTS

FIELD OF THE INVENTION

The invention relates generally to DnaK inhibiting agents. More specifically, the invention relates to natural peptide DnaK inhibitors, and analogs thereof, in combination with known antibacterial agents to elicit an enhanced inhibitory effect upon bacterial growth and/or bacteriocidal activity.

BACKGROUND OF THE INVENTION

The continuing search for new and effective antibacterial agents that can treat infections caused by organisms that are increasingly resistant to known classes of antibacterial agents has identified a plethora of potential next generation antibiotics. Many of these agents have subsequently been shown to demonstrate either poor physiochemical properties, an increased tendency to induce bacterial resistance, poor toxicological profiles, or low efficacy in vivo. Over the past decade or so, certain antibacterial peptides and glycopeptides isolated from insects have been noted as promising candidates for drug development programs (see, e.g., Hultmark, *Trends Genet.*, 9:178-183 (1993); Gillespie et al., *Annu. Rev. Entomol.*, 42:611-6443 (1997); Otvos, Jr. et al., *Protein Science* 9:742 (2000); International Patent Publication No. WO 94/05787, published Mar. 17, 1994; French Patent No. 2733237, granted Oct. 25, 1996; International Patent Publication No. WO 99/05270, published Feb. 4, 1999; International Patent Publication No. WO 97/30082, published Aug. 21, 1997; French Patent No. 2695392, granted Mar. 11, 1994; French Patent No. 2732345, granted Oct. 4, 1996; and International Patent Publication No. WO 00/78956, published Dec. 28, 2000.)

While many antibacterial peptides from other origins kill bacteria by disrupting the cell membrane or cell wall of the bacteria, a subset of the insect-derived antibacterial peptides have an unusual mode of action, i.e., they inhibit the bacterial chaperone protein DnaK. Two such peptides are drosocin, a 19 amino acid residue peptide from *Drosophila* (Bulet et al., *J. Biol. Chem.* 268:14893-14897 (1993)) and pyrrhocoricin, a 20 amino acid residue peptide from *Pyrrhocoris* (Cociancich et al, *Biochem. J.* 300:567-575 (1994)). Drosocin and pyrrhocoricin are glycopeptides characterized by the presence of a disaccharide in the mid-chain position. The presence of the disaccharide increases the in vitro antibacterial activity of drosocin, but decreases the activity of pyrrhocoricin (Bulet et al., supra; Hoffmann et al., *Biochim. Biophys. Acta,* 1426:459-467 (1999)).

While active in vitro, both drosocin and pyrrhocoricin are known to be highly susceptible to proteolytic degradation in the presence of mammalian serum. Both aminopeptidase and carboxypeptidase cleavage products are observed. Metabolites lacking as few as five amino terminal or two carboxy terminal amino acids have been shown to be inactive as antibacterial agents in vitro (Bulet et al., supra; Hoffmann et al., supra).

The interaction of non-glycosylated pyrrhocoricin with bacterial DnaK has been extensively studied (see, e.g., Otvos, Jr. et al, *Biochemistry* 39:14150-14159 (2000); Kragol et al., *Biochemistry* 40:3016-3026 (2001)). Residues within the N-terminal half of the peptide have been implicated in binding to DnaK, and were shown to specifically interact with helices D and E of the helical lid of the bacterial protein (Kragol et al., *Eur. J. Biochem.* 269:4226-4237 (2002)).

DnaK has been demonstrated to be the central protein in a multiprotein bacterial chaperone system including the chaperone protein DnaK and a variety of co-chaperone proteins such as DnaJ and GrpE. The co-chaperone proteins are essential to the efficient physiological processing of both natural and unnatural substrates. One role for this chaperone system is to catalyze the refolding of either unfolded or misfolded bacterial proteins, as is evident from the role of this system in the heat-shock response. An additional role of the DnaK chaperone system is the regulation of gene expression through the processing of specific RNA polymerase subunits.

DnaK deletion mutants of many organisms have been generated and overall the mutant strains have been shown to exhibit lower growth rates, greater susceptibility to environmental stress, reduced viability in cellular environments, and reduced ability to establish infections in vivo compared to the wild-type strains.

The susceptibility of DnaK deletion mutants to known antibacterial agents has been only briefly examined. Wolska et al. (*Microb. Drug Resist.* 6:119-126 (2000)) have shown that an *E. coli* DnaJ deletion mutant and the corresponding DnaK/DnaJ double deletion mutant were not more susceptible to ampicillin, chloramphenicol or tetracycline under routine conditions. Conversely, Yamaguchi et al. (*BMC Microbiol.* 3:16 (2003)) demonstrated a moderate increase in susceptibility of an *E. coli* DnaK deletion mutant to levofloxacin.

While the role of the DnaK chaperone system in bacterial growth and survival is only now starting to be appreciated and understood, the role and utility of DnaK inhibitors as antibacterial agents is not well established. Accordingly, there is a need to investigate and exploit the useful therapeutic activities of DnaK inhibitors, including pyrrhocoricin, drosocin and their analogs.

SUMMARY OF THE INVENTION

Applicants have invented compositions, methods, and kits for inhibiting the growth of bacteria comprising a DnaK inhibitor and a known antibacterial agent. Applicants have discovered that coadministration of such agents enhances the antibacterial potential of the DnaK inhibitor, the known antibacterial agent, or both. Such coadministration to patients suffering from a bacterial infection has the possible benefit of i) lowering the necessary therapeutically effective dose; ii) extending the duration of activity of a fixed dose; iii) reducing the likelihood of the development of resistant strains of the infecting organism; and/or iv) expanding the spectrum of activity of the individual agents. Agents that exhibit a therapeutic synergistic effect when coadministered are preferred.

Accordingly, one aspect of the present invention is directed to a method for treating a bacterial infection comprising coadministering to a patient in need of such treatment
  (a) a therapeutically effective amount of a DnaK inhibitor; and
  (b) a therapeutically effective amount of a known antibacterial agent.

In some embodiments, the DnaK inhibitor is pyrrhocoricin, drosocin or an analog thereof, while the known antibacterial agent is an antibiotic from the fluoroquinolone, β-lactam, tetracycline, macrolide, aminoglycoside, glycopeptide, or folic acid synthesis inhibitor family of antibiotics. Preferably, the DnaK inhibitor and antibiotic provide a therapeutic synergistic effect.

In various embodiments, the compositions are administered orally, parenterally, topically, rectally or intranasally. Preferred routes of administration are oral and parenteral administration. The individual agents can be administered either substantially simultaneously or sequentially by the same route, either in a single dosage form or as separate dosage forms, or by separate routes.

Another aspect of the present invention is directed to a pharmaceutical composition for treating a bacterial infection, comprising:

(a) a therapeutically effective amount of a DnaK inhibitor; and
(b) a therapeutically effective amount of a known antibacterial agent.

The pharmaceutical compositions generally further comprise one or more pharmaceutically acceptable carriers. Preferred routes of administration for the pharmaceutical compositions are oral and parenteral.

Another aspect of the present invention is directed to a kit for treating a bacterial infection comprising a container that contains (a) a therapeutically effective amount of a DnaK inhibitor; and
(b) a therapeutically effective amount of a known antibacterial agent.

In some embodiments, the kit further comprises other apparatus and media for administering the agents to a patient, as well as instructions for using the kit to treat a bacterial infection.

DETAILED DESCRIPTION OF THE INVENTION

Figure 1:
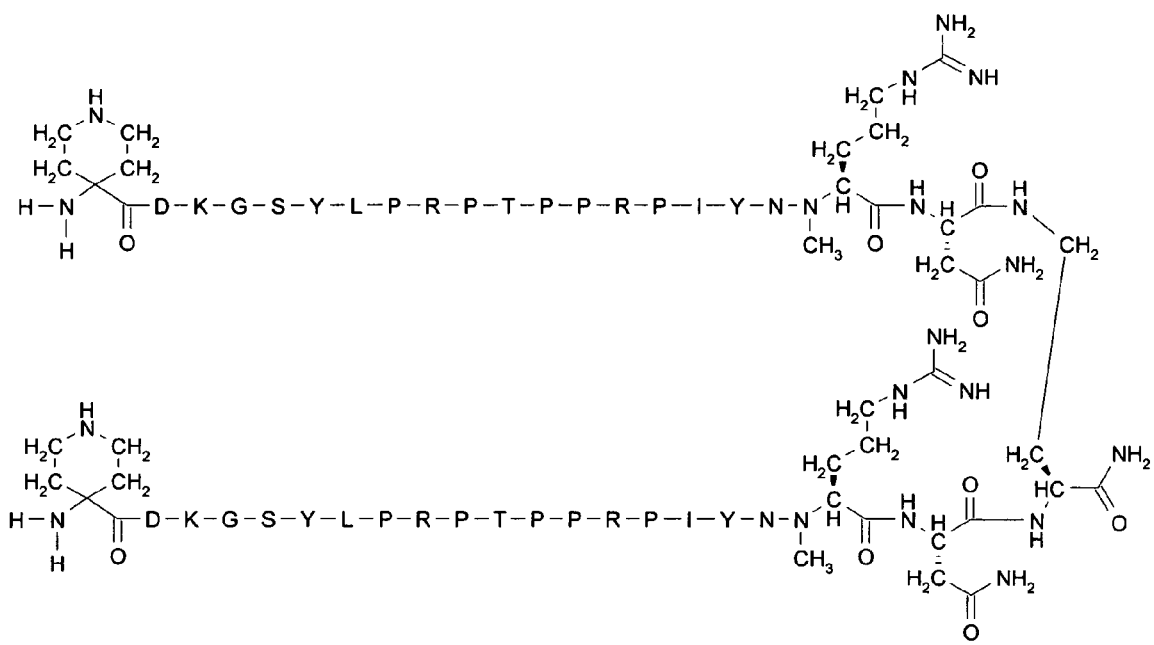
FIG. 1 shows the structure of CHP-105, a typical peptide inhibitor of *E. coli* DnaK.

The term "bacterial infection" refers to an infection resulting from the invasion of the body by bacteria. The infection may or may not be clinically apparent. The terms "bacteria", "bacterium" and "bacterial" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces,* and *Rickettsia*. All forms of bacteria are included within this definition including cocci, bacilli, spirochetes, spheroplasts, protoplasts, etc. Also included within this term are prokaryotic organisms that are Gram negative or Gram positive.

The term "antibacterial agent" as used herein refers to any substance of natural, semisynthetic or synthetic origin, including all known antibiotics, that kills or inhibits the growth of one or more bacteria, but causes little or no host damage.

The terms "enhance" and "enhancement" as used herein refer to an increase in the therapeutic activity (whether in vitro or in vivo) of a therapeutic agent (e.g., a DnaK inhibitor) when used in combination with another therapeutic agent (e.g., a known antibacterial agent), whether additive or synergistic. Such therapeutic effects include, e.g., bacteriostatic activity, bacteriocidal activity, therapeutic efficacy, and therapeutic safety. The term "inhibiting bacterial growth" is intended to cover both bacteriostatic and bacteriocidal activities.

The term "additive" as used herein refers to the combined effect of administering two therapeutic agents, where the overall response is equal to, or nearly equal to, the sum of the responses if the agents were administered as monotherapy. The terms "synergy", "therapeutic synergy" and "synergistic" as used herein refer to the combined effect of administering two therapeutic agents, where the overall response is greater than the sum of the two individual effects. The term synergy also refers to the combined effect of administering an amount of one therapeutic agent that, when administered as monotherapy, produces no measurable response but, when administered in combination with another therapeutic compound, produces an overall response that is greater than that produced by the second compound alone.

The term "patient" as used herein includes both human and other animals. The term "animals" as used herein refers to humans and other animals.

The terms "treating" and "treatment" of a state, disorder, disease or condition as used herein refers to (1) preventing or delaying the appearance of clinical symptoms of the state, disorder, disease or condition developing in a patient that may be afflicted with or predisposed to the state, disorder, disease or condition but does not yet experience or display clinical or subclinical symptoms of the state, disorder or condition, (2) inhibiting the state, disorder, disease or condition, i.e., arresting or reducing the development of the disease or at least one clinical or subclinical symptom thereof, or (3) relieving the disease, i.e., causing regression of the state, disorder or condition or at least one of its clinical or subclinical symptoms. The benefit to a patient to be treated is either statistically significant or at least perceptible to the patient and/or to the physician.

The terms "effective amount" and "therapeutically effective amount" as used herein refer to the amount of a compound that, when administered to a patient for treating a state, disorder, disease or condition, is sufficient to effect such treatment. The effective amount or therapeutically effective amount will vary depending on the compound, the disease and its severity, and the age, weight, physical condition and responsiveness of the individual to be treated.

The terms "delivering" and "administering" as used herein refer to providing a therapeutically effective amount of an active agent to a particular location or locations within a patient causing a therapeutically effective concentration of the active ingredient at the particular location or locations. This can be accomplished, e.g., by local or by systemic administration of the active ingredient to the host.

The term "coadministration" as used herein refers to the administration of a therapeutically effective amount of a first active agent (e.g., a DnaK inhibitor) and a therapeutically effective amount of a second active agent (e.g., a known antibacterial agent) to a patient. Coadministration encompasses administration of the first and second agents in an essentially simultaneous manner, such as in a single pharmaceutical composition, for example, capsule or tablet having a fixed ratio of first and second amounts, or in multiple, separate capsules or tablets for each. In addition, coadministration also encompasses use of each agent in a sequential manner in either order. When coadministration involves the separate administration of each agent, the agents are administered sufficiently close in time to have the desired therapeutic effect.

The term "pharmaceutically acceptable" as used herein refers to those active agents, salts and esters, and excipients which are, within the scope of sound medical judgment, suitable for use in contact with the tissues of humans and lower animals without undue toxicity, irritation, allergic response and the like, commensurate with a reasonable benefit/risk ratio, and effective for their intended use.

The term "composition" as used herein refers to a product comprising the specified agent or agents, as well as any product which results, directly or indirectly, from combination of the specified ingredients. A "pharmaceutical composition" is intended to include the combination of an active agent or agents with a carrier, inert or active, making the composition suitable for diagnostic or therapeutic use in vivo, in vitro or ex vivo. The compositions can also include stabilizers, preservatives, adjuvants, fillers, flavors and other excipients.

The term "alkyl" as used herein refers to a saturated aliphatic radical containing from one to ten carbon atoms or a mono- or polyunsaturated aliphatic hydrocarbon radical containing from two to twelve carbon atoms, the mono- or polyunsaturated aliphatic hydrocarbon radical containing at least one double or triple bond, respectively. Alkyl refers to both branched and unbranched alkyl groups. Examples of alkyl include alkyl groups which are straight chain alkyl groups containing from one to eight carbon atoms and branched alkyl groups containing from three to eight carbon atoms. Other examples include lower alkyl groups which are straight chain alkyl groups containing from one to six carbon atoms and branched alkyl groups containing from three to six carbon atoms. It is understood that any combination term using an "alk" or "alkyl" prefix refers to analogs according to the above definition of "alkyl". For example, terms such as "alkoxy" and "alkythio" refer to alkyl groups linked to a second group via an oxygen or sulfur atom. "Alkanoyl" refers to an alkyl group linked to a carbonyl group. Each alkyl or alkyl analog described herein shall be understood to be optionally partially or fully halogenated.

The term "cycloalkyl" refers to the cyclic analog of an alkyl group, as defined above. Examples of cycloalkyl groups are saturated or unsaturated nonaromatic cycloalkyl groups containing from three to eight carbon atoms, and other examples include cycloalkyl groups having three to six carbon atoms. Each cycloalkyl described herein shall be understood to be optionally partially or fully halogenated. The term "halogen" refers to a halogen radical selected from fluoro, chloro, bromo or iodo.

The term "heterocycle" refers to a stable 4-8 membered (but preferably, 5 or 6 membered) monocyclic or 8-11 membered bicyclic heterocycle radical which may be either saturated or unsaturated. Each heterocycle consists of carbon atoms and from 1 to 4 heteroatoms chosen from nitrogen, oxygen and sulfur. The heterocycle may be attached by any atom of the cycle, which results in the creation of a stable structure. Unless otherwise specified, the term "heterocycle", when associated with another moiety, shall have the same meaning as given above.

The term "aryl" as used herein means an aromatic monocyclic or multicyclic ring system comprising about 6 to about 14 carbon atoms, preferably about 6 to about 10 carbon atoms. The term "arylalkyl" refers to aryl-alkyl, where aryl and alkyl are defined above.

The term "aroyl" means an aryl-C(O)— group in which the aryl group is as previously described. The bond to the parent moiety is through the carbonyl.

The term "acetyl" as used herein refers to $CH_3C(O)$—.

The term "positively charged reporter group" as used herein includes any reporter that can be attached to the N-termini of a DnaK peptide inhibitor, such as, e.g., fluorescein-Lys-Val and fluorescein-Lys. Other such reporters may be readily selected from compositions known and available to those skilled in the art.

The present invention relates to the treatment of various bacterial infections by coadministration of (a) a therapeutically effective amount of a DnaK inhibitor; and (b) a therapeutically effective amount of a known antibacterial agent.

Examples of DnaK inhibitors for use in the present invention include DnaK peptide inhibitors, such as, e.g., pyrrhocoricin (Val-Asp-Lys-Gly-Ser-Tyr-Leu-Pro-Arg-Pro-Thr-Pro-Pro-Arg-Pro-Ile-Tyr-Asn-Arg-Asn; SEQ ID NO: 4), drosocin (Gly-Lys-Pro-Arg-Pro-Tyr-Ser-Pro-Arg-Pro-Thr-Ser-His-Pro-Arg-Pro-Ile-Arg-Val; SEQ ID NO: 5) and active analogs thereof. The DnaK inhibitors can be provided by conventional peptide synthesis or by recombinant DNA means. For example, pyrrhocoricin and various analogs thereof can be provided as described in Otvos, Jr., supra and WO 00/78956.

In specific embodiments, the DnaK inhibitor is an analog of pyrrhocoricin having the formula $R^1$-SEQ ID NO: 1-$R^2$, wherein SEQ ID NO: 1 is Asp-Lys-Gly-Ser-Tyr-Leu-Pro-Arg-Pro-Thr-Pro-Pro-Arg-Pro-Ile-Tyr-Asn-$R^3$-, $R^1$ adds a net positive charge to the N-terminus of said peptide and is selected from the group consisting of
  (a) a straight chain, branched, cyclic or heterocyclic alkyl group;
  (b) a straight chain, branched, cyclic or heterocyclic alkanoyl group;
  (c) a positively charged reporter group;
  (d) a sequence of additional amino acids selected from the group consisting of Arg-Val, Lys-Val, Val and Lys-Val-Asp-Lys-Val (SEQ ID NO: 2), 1-amino-1-carboxycyclohexane and 4-amino-4-carboxypiperidine, wherein the N-terminal additional amino acid is optionally substituted by one or more of (a), (b), or (c); and
  (e) an additional amino acid sequence Arg-Pro-Pro-Thr-Pro-Arg-Pro-Leu-Lys-Val (SEQ ID NO: 3) that cyclizes the peptide by bridging between the N— and C-termini thereof, $R^2$ is selected from the group consisting of
  (a) a free hydroxyl, an amide, an imide, or a sugar; and
  (b) an additional amino acid selected from the group consisting of Asn, D-Asn, Asp, Asn substituted by a member selected from the group consisting of a free hydroxyl, an amide, an imide, and a sugar, and Asp substituted by a member selected from the group consisting of a free hydroxyl, an amide, an imide and a sugar, and $R^3$ is selected from the group consisting of arginine or N-alkylarginine, wherein alkyl represents a 1-6 carbon saturated chain.

In more specific embodiments, the DnaK inhibitor is an analog of pyrrhocoricin having the above-described formula $R^1$-SEQ ID NO: 1-$R^2$, wherein $R^2$ is Asn-$R^4$, $R^4$ is selected from the group consisting of
  (a) a free hydroxyl, an amide, an imide, or a sugar; and
  (b) a substituted amino acid represented by structural formula I

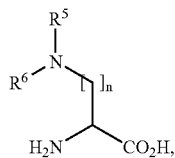

$R^5$ is selected from alkanoyl, aroyl or arylalkanoyl, $R^6$ is hydrogen or alkyl and n=1-4.

In still more specific embodiments, the DnaK inhibitor is an analog of pyrrhocoricin having the above-described formula $R^1$-SEQ ID NO: 1-$R^2$, wherein $R^1$ is selected from the group consisting of valine, 1-amino-1-carboxycyclohexane, 4-amino-4-carboxypiperidine, $R^2$ is as above, $R^3$ is selected from the group consisting of arginine and N-alkylarginine, $R^4$ is a substituted amino acid represented by structural formula I, $R^5$ is selected from the group consisting of acetyl and $R^1$-SEQ ID NO: 1-$R^3$, $R^6$ is hydrogen and n=1 or 2.

In preferred embodiments, the DnaK inhibitor is an analog of pyrrhocoricin termed CHP-105 (structure shown in FIG. 1) having the above-described formula $R^1$-SEQ ID NO: 1-$R^2$, wherein $R^1$ is 4-amino-4-carboxypiperidine, $R^2$ is as above, $R^3$ is N-methylarginine, $R^4$ is a substituted amino acid represented by structural formula I, wherein $R^5$ is $R^1$-SEQ ID NO: 1-$R^3$, $R^6$ is hydrogen and n=2.

Any known antibacterial agent can be used in the present invention. Preferably, the known antibacterial agent is an antibiotic. These include, e.g., antibiotics from the fluoroquinolone, β-lactam, tetracycline, macrolide, aminoglycoside, glycopeptide, or folic acid synthesis inhibitor family of inhibitors. Examples of particular antibiotics include, e.g., linezolid, amikacin, gentamicin, tobramycin, imipenem, meropenem, cefotetan, cefoxitin, cefuroxime, cefoperazone, cefotaxime, ceftazidime, ceftozoxime, ceftriaxone, cefepime, azithromycin, ampicillin, mezlocillin, piperacillin, ticarcillin, ciprofloxacin, levofloxacin, alatrofloxacin, gatifloxacin, minocycline, chloramphenicol, clindamycin, vancomycin, cefazolin, penicillin G, nafcillin, ofloxacin, and oxacillin. The particular antibiotic chosen may depend on the specific bacterial infection presented to the clinician.

The DnaK inhibitors and known antibacterial agents of the present invention may form salts which are also within the scope of the present invention. Reference to these agents is therefore understood to include reference to salts thereof, unless otherwise indicated. The term "salt(s)" as used herein, denotes acidic salts formed with inorganic and/or organic acids, as well as basic salts formed with inorganic and/or organic bases. All such acid salts and base salts are intended to be pharmaceutically acceptable salts, and all acid and base salts are considered equivalent to the free forms of the corresponding agents for purposes of the present invention.

It is also understood that each of the agents described above may also be prodrug form. The term "prodrug" as used herein refers to a derivative of a drug molecule that requires a chemical or enzymatic biotransformation in order to release the active parent drug in the body.

In addition, all stereoisomers (for example, geometric isomers, optical isomers and the like) of the agents described above (including those of salts and solvates), such as those which may exist due to asymmetric carbons on various substituents, including enantiomeric forms (which may exist even in the absence of asymmetric carbons), rotameric forms, atropisomers, and diastereomeric forms, are contemplated within the scope of the present invention. Individual stereoisomers may, for example, be substantially free of other isomers, or may be admixed, for example, as racemates or with all other, or other selected, stereoisomers. The chiral centers can have the S or R configuration as defined by the IUPAC 1974 Recommendations. The use of the terms "salt", "solvate" and the like, is intended to equally apply to the salt and solvate of enantiomers, stereoisomers, rotamers, tautomers or racemates of the present agents.

Methods for identifying specific combinations of Dnak inhibitors and known antibacterial agents for coadministration treatment are well known in the art. These methods include both in vitro methods, such as the bacterial growth inhibition assay described in Example 1, and in vivo methods, such as those involving various well-known experimental mouse infection models. Although a synergistic effect is preferred, an additive effect may still indicate that the combination of DnaK inhibitor and known antibacterial agent is therapeutically useful.

In therapeutic use for treating bacterial infections, the DnaK inhibitor and the known antibacterial agent are coadministered to a patient in need of such treatment. Examples of bacterial infections that can be treated by the compositions, methods and kits of the present invention include infections resulting from bacteria of the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus, Bordetella* and *Francisella*.

The actual dosages of the DnaK inhibitor and the known antibacterial agent employed in the treatment may be varied depending upon the requirements of the patient and the severity of the condition being treated. Determination of the proper dosage regimen for a particular situation is within the skill of the art. The amount and frequency of administration of the DnaK inhibitor and the known antibacterial agent will be regulated according to the judgment of the attending clinician considering such factors as age, condition and size of the patient as well as severity of the symptoms being treated.

The DnaK inhibitor and the known antibacterial agent can be administered orally, parenterally, topically, rectally, or intranasally, either substantially simultaneously or sequentially. Preferred routes of administration are oral and intravenous administration. Each of the agents can be administered by the same route (e.g., injection), either in a single dosage form or as separate dosage forms, or by separate routes (e.g., orally and parenterally).

Parenteral administrations include injections to generate a systemic effect or injections directly to the afflicted area. Examples of parenteral administrations are subcutaneous, intravenous, intramuscular, intradermal, intrathecal, intraocular, intravetricular, and general infusion techniques.

Topical administrations include the treatment of infectious areas or organs readily accessibly by local application, such as, e.g., eyes, ears including external and middle ear infections, vaginal, open and sutured or closed wounds, and skin. Topical administrations also include transdermal delivery to generate a systemic effect.

Rectal administrations include, e.g., the form of suppositories. Intranasal administrations include, e.g., nasal aerosol and inhalation applications.

Pharmaceutical compositions for simultaneous coadministration of a DnaK inhibitor and a known antibacterial agent may be prepared by methods well known in the art, including, e.g., conventional mixing, dissolving, granulation, dragee-making, levigating, emulsifying, encapsulating, entrapping, lyophilizing processes, and spray drying.

Pharmaceutical compositions may be formulated in a conventional manner using one or more physiologically acceptable carriers including, e.g., excipients and auxiliaries that facilitate processing of the active agents into preparations that can be used pharmaceutically. Proper formulation is dependent upon the route of administration chosen.

For oral administration, agents can be formulated by combining active compounds with pharmaceutically acceptable carriers well known in the art. Such carriers enable the agents to be formulated as tablets, pills, lozenges, dragees, capsules, liquids, solutions, emulsions, gels, syrups, slurries, suspensions and the like, for oral ingestion by a patient. A carrier can be at least one substance that may also function, for example, as a diluent, flavoring agent, solubilizer, lubricant, suspending agent, binder, tablet disintegrating agent, or encapsulating agent. Examples of such carriers or excipients include, e.g., magnesium carbonate, magnesium stearate, talc, sugar, lactose, sucrose, pectin, dextrin, mannitol, sorbitol, starches, gelatin, cellulosic materials, low melting wax, cocoa butter or powder, polymers such as polyethylene glycols, and other pharmaceutical acceptable materials.

Dragee cores are preferably provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for uses including, for example, identification and characterization of different combinations of active compound doses.

Pharmaceutical compositions that can be used orally include, for example, push-fit capsules made of gelatin, as well as soft, sealed capsules made of gelatin and a plasticizer (e.g., glycerol and sorbitol). The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, liquid polyethylene glycols, cremophor, capmul, medium or long chain mono-, di- or triglycerides. Stabilizers may also be added in these formulations.

Liquid form compositions include, for example, solutions, suspensions, and emulsions. For example, there may be provided solutions of compounds disclosed in the present application dissolved in water and water-propylene glycol and water-polyethylene glycol systems, optionally containing suitable conventional coloring agents, flavoring agents, stabilizers, and thickening agents.

Agents may also be formulated for parenteral administration, including, for example, injections, bolus injections, and continuous infusion. Formulations for parenteral administration may be presented in unit dosage form including, for example, ampoules and multi-dose containers, optionally with an added preservative. The compositions may take such forms as suspensions, solutions or emulsions in oily or aqueous vehicles, and may contain formulating materials such as suspending, stabilizing, and/or dispersing agents.

For injection, agents are preferably formulated in aqueous solution, preferably in physiologically compatible buffers or physiological saline buffer. Suitable buffering agents include, e.g. trisodium orthophosphate, sodium bicarbonate, sodium citrate, N-methylglucamine, L(+)-lysine and L(+)-arginine. Solutions of the active agents can be optionally mixed with a nontoxic surfactant. Dispersions can also be prepared in glycerol, liquid polyethylene glycols, triacetin, and mixtures thereof, and in oils. Under ordinary conditions of storage and use, these preparations may contain a preservative to prevent the growth of microorganisms.

Pharmaceutical dosage forms suitable for injection or infusion include, for example, sterile aqueous solutions or dispersions, or sterile powders including the active agent or agents that are adapted for the extemporaneous preparation of sterile injectable or infusible solutions or dispersions, optionally encapsulated in liposomes. In all cases, the ultimate dosage form is preferably sterile, fluid, and stable under the conditions of manufacture and storage. The proper fluidity can be maintained, for example, by the formation of liposomes, by the maintenance of the required particle size in the case of dispersions, or by the use of surfactants. In many cases, it will be preferable to include isotonic agents including, for example, sugars, buffers, or sodium chloride. Prolonged absorption of the injectable compositions can be brought about by the use of agents to delay absorption (e.g., aluminum monostearate, gelatin) in the compositions.

Sterile injectable solutions can be prepared by incorporating the active agent or agents in the required amount in the appropriate solvent with optional ingredients as required (e.g., as enumerated above), followed by, for example, filter sterilization. In the case of sterile powders for the preparation of sterile injectable solutions, preferred methods of preparation include, for example, vacuum drying and freeze drying techniques, which yield a powder of the active ingredient plus any additional desired ingredient present in the previously sterile-filtered solutions.

Other parenteral administrations also include aqueous solutions of a water-soluble form, such as, without limitation, a salt, of the active agent or agents. Additionally, suspensions of the active agents may be prepared in a lipophilic vehicle. Suitable lipophilic vehicles include, for example, fatty oils such as sesame oil, synthetic fatty acid esters such as ethyl oleate and triglycerides, and materials such as liposomes. Aqueous injection suspensions preferably contain substances that increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

For suppository administration, agents may be formulated by mixing the agent with a suitable non-irritating excipient that is solid at room temperature but liquid at rectal temperature, which will therefore melt in the rectum to release the drug. Such materials include, for example, cocoa butter, beeswax, and other glycerides.

For administration by inhalation, agents are preferably conveniently delivered through an aerosol spray in the form of solution, dry powder, or cream. The aerosol may use, for example, a pressurized pack or a nebulizer and a suitable propellant. In the case of a pressurized aerosol, the dosage unit may be controlled by providing a valve to deliver a metered amount. Capsules and cartridges of, e.g., gelatin for use in an inhaler may be formulated containing a power base such as lactose or starch.

For topical applications, a pharmaceutical composition may be formulated in a suitable ointment containing the active agents suspended or dissolved in one or more carriers. Carriers for topical administration of the agents include, e.g., mineral oil, liquid petrolatum, white petrolatum, propylene glycol, polyoxyethylene, polyoxypropylene compound, emulsifying wax, and water. Aternatively, the pharmaceutical compositions can be formulated in suitable lotions, including, for example, suspensions, emulsions, and creams containing the active components suspended or dissolved in one or more pharmaceutically acceptable carriers. Suitable carriers include, e.g., mineral oil, sorbitan monostearate, polysorbate 60, cetyl esters wax, ceteary alcohol, 2-octyldodecanol, benzyl alcohol, and water.

For ophthalmic and otitis uses, pharmaceutical compositions may be formulated as micronized suspensions in isotonic, pH adjusted sterile saline, or preferably, as solutions in isotonic, pH adjusted sterile saline, either with or without a preservative such as benzylalkonium chloride. Alternatively, for ophthalmic uses, pharmaceutical compositions may be formulated in an ointment such as petrolatum.

In addition to the formulations described previously, the agents may also be formulated as depot preparations. Such long acting formulations may be in the form of implants. Agents may be formulated for this route of administration with suitable polymers, hydrophobic materials, or as a sparing soluble derivative such as, without limitation, a sparingly soluble salt.

Additionally, agents may be delivered using a sustained-release system. Various sustained-release materials have been established and are well known by those skilled in the art. Sustained-release capsules may, depending on their chemical nature, preferably release the compounds for up to about 24 hours, and more preferably for up to several days. Depending on the chemical nature and the biological stability of the therapeutic agent, additional strategies for protein stabilization may be employed.

The DnaK inhibitor and the known antibacterial agent can be provided in kit form for coadministration to a patient suffering from a bacterial infection. The arrangement and construction of such kits are well known to those skilled in the art. Such kits may include a container for containing the individual agents or pharmaceutical compositions, as well as other apparatus and media for administering the agents, such as, e.g., syringes, buffers, diluents, etc. The kits generally also include instructions for using the kit to treat a bacterial infection.

Those of skill in the art will recognize that the compositions, methods and kits of the present invention can also be used for the sterilization of human and animal food products.

Specific embodiments of the present invention will now be described in the following Examples. The Examples are illustrative only, and are not intended to limit the remainder of the disclosure in any way.

EXAMPLES

Example 1

Figure 2:
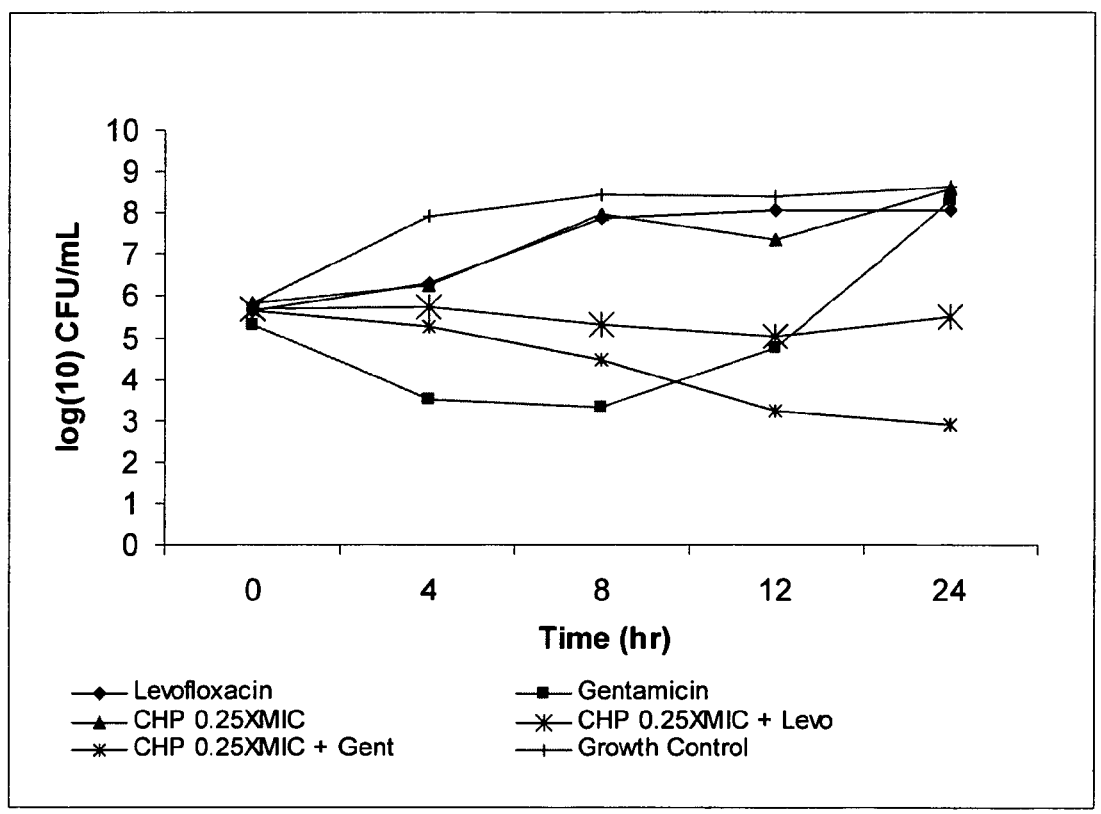
FIG. 2 shows the enhanced rate of antibacterial activity of a combination of 16 µg/ml CHP-105 and levofloxacin or gentamicin when administered to rapidly growing *E. coli*.
Figure 3:
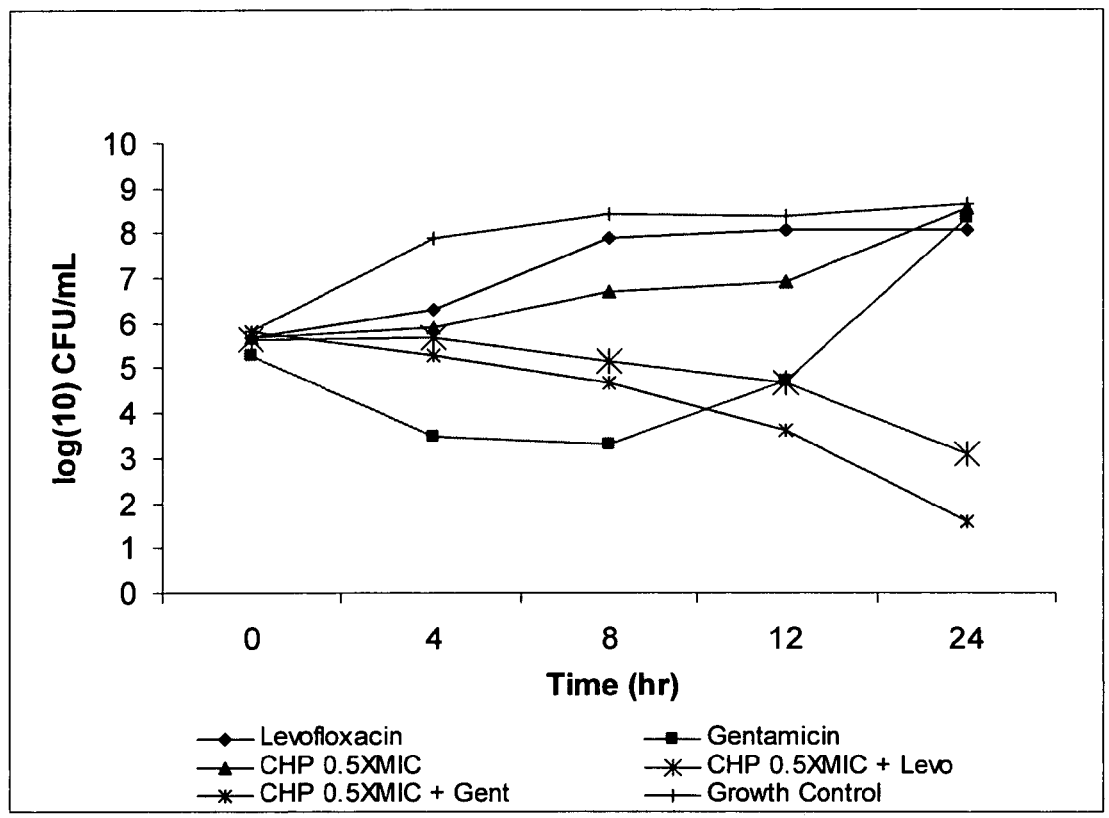
FIG. 3 shows the enhanced rate of antibacterial activity of a combination of 32 µg/ml CHP-105 and levofloxacin or gentamicin when administered to rapidly growing *E. coli*.
Figure 4:
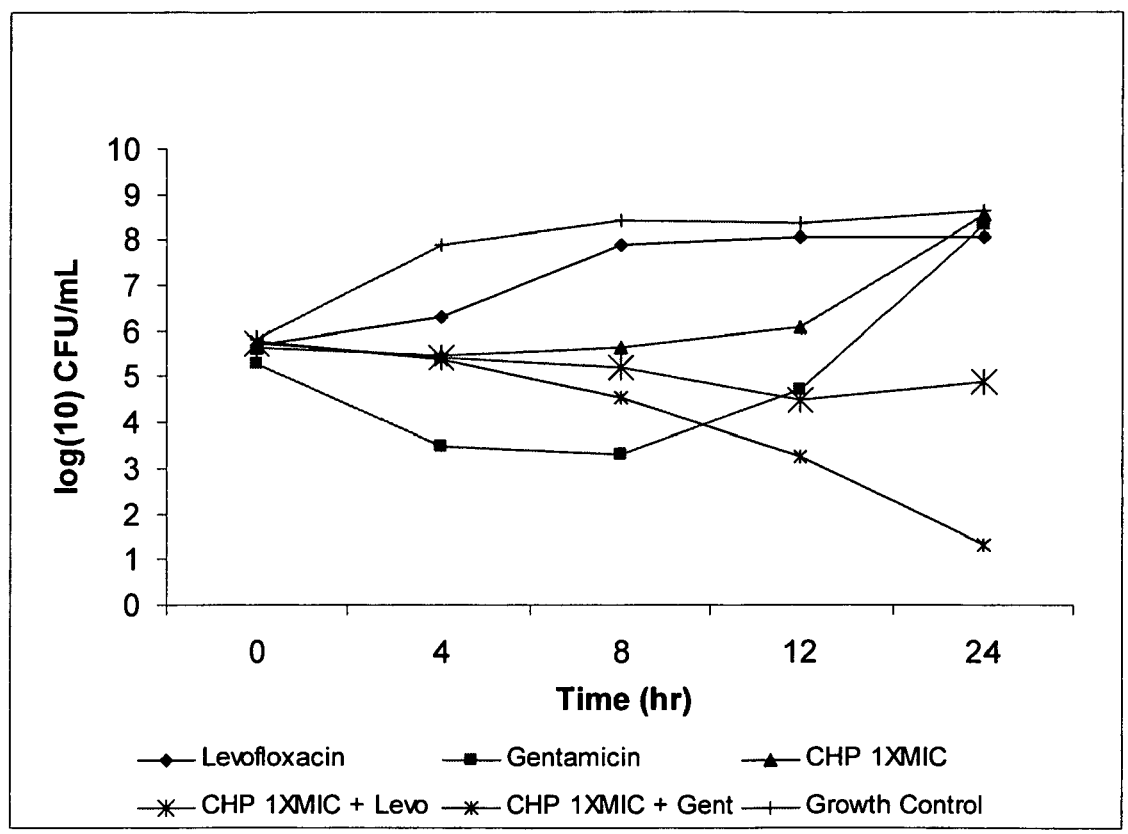
FIG. 4 shows the enhanced rate of antibacterial activity of a combination of 64 µg/ml CHP-105 and levofloxacin or gentamicin when administered to rapidly growing *E. coli*.
Figure 5:
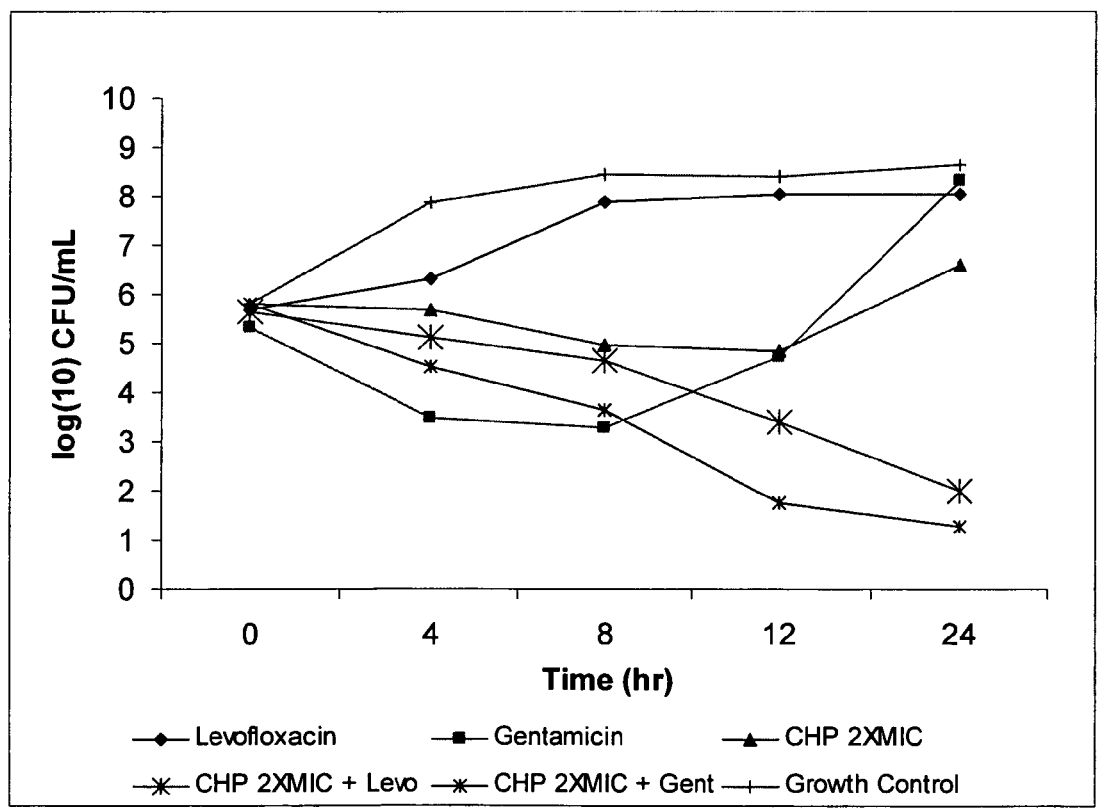
FIG. 5 shows the enhanced rate of antibacterial activity of a combination of 128 µg/ml CHP-105 and levofloxacin or gentamicin when administered to rapidly growing *E. coli*.
Figure 6:
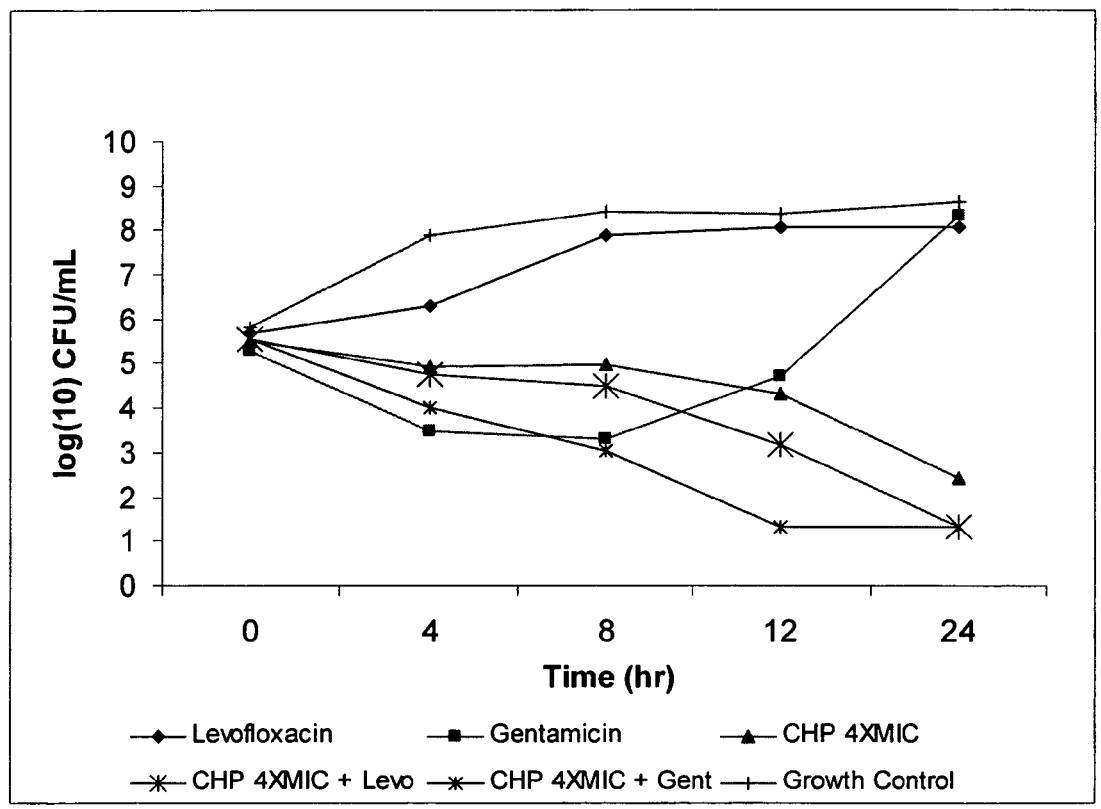
FIG. 6 shows the enhanced rate of antibacterial activity of a combination of 246 µg/ml CHP-105 and levofloxacin or gentamicin when administered to rapidly growing *E. coli*.

Growth inhibition assays were performed using the Gram negative *E. coli* isolate CHP-04-002EC obtained from Laboratory Specialists, Inc. (Westlake, Ohio). DnaK inhibitor CHP-105 (structure shown in FIG. 1) at concentrations of 16 μg/ml (0.25×MIC; FIG. 2), 32 μg/ml (0.5×MIC; FIG. 3), 64 μg/ml (1×MIC; FIG. 4), 128 μg/ml (2×MIC; FIG. 5) and 256 μg/ml (4×MIC; FIG. 6) were applied to midlogarithmic phase bacterial culture, either alone or in combination with levofloxacin (0.125 μg/ml; 0.25×MIC) or gentamicin (0.06 μg/ml; 0.25×MIC). Untreated bacterial culture served as growth control. At 4, 8, 12 and 24 hrs post-application, the cultures were serially diluted, plated and allowed to grow overnight. Colony forming units (CFU) were determined by counting the number of newly grown colonies and multiplying by the dilution factor. A >1 log decrease in CFU compared to the most active single agent is considered additive, while a >2 log decrease in CFU is considered synergistic.

As can be seen in FIGS. 2-6, the coadministration of CHP-105 with levofloxacin or gentamicin enhanced the antibacterial effect of either agent alone (both additively and synergistically), particularly at later time points and lower CHP-105 concentrations. The combinations of 16 μg/ml CHP-105 with levofloxacin produced synergistic decreases of 2.66, 2.28 and 2.55 CFU at 8, 12 and 24 hrs, respectively, compared to the most active single agent (FIG. 2). The combination of 16 μg/ml CHP-105 with gentamicin produced an additive decrease of 1.48 CFU at 12 hrs and a synergistic decrease of 5.39 CFU at 24 hrs, compared to the most active single agent (FIG. 2).

The combinations of 32 μg/ml CHP-105 with levofloxacin produced an additive decrease of 1.5 CFU at 8 hrs and synergistic decreases of 2.26 and 4.96 CFU at 12 and 24 hrs, respectively, compared to the most active single agent (FIG. 3). The combination of 32 μg/ml CHP-105 with gentamicin produced an additive decrease of 1.11 CFU at 12 hrs and a synergistic decrease of 6.70 CFU at 24 hrs, compared to the most active single agent (FIG. 3).

The combinations of 64 μg/ml CHP-105 with levofloxacin produced an additive decrease of 1.59 CFU at 12 hrs and a synergistic decrease of 3.15 CFU at 24 hrs, respectively, compared to the most active single agent (FIG. 4). The combination of 64 μg/ml CHP-105 with gentamicin produced an additive decrease of 1.46 CFU at 12 hrs and a synergistic decrease of 7.01 CFU at 24 hrs, compared to the most active single agent (FIG. 4).

The combinations of 128 μg/ml CHP-105 with levofloxacin produced an additive decrease of 1.41 CFU at 12 hrs and a synergistic decrease of 4.59 CFU at 24 hrs, respectively, compared to the most active single agent (FIG. 5). The combination of 128 μg/ml CHP-105 with gentamicin produced synergistic decreases of 2.94 and 5.29 CFU at 12 and 24 hrs, respectively, compared to the most active single agent (FIG. 5).

The combinations of 264 μg/ml CHP-105 with levofloxacin produced an additive decrease of 1.13 and 1.11 CFU at 12 and 24 hrs, respectively, compared to the most active single agent (FIG. 6). The combination of 264 μg/ml CHP-105 with gentamicin produced an additive decrease of 1.11 CFU at 24 hrs, compared to the most active single agent (FIG. 6). Collectively, these results demonstrate that the combination of a DnaK inhibitor and a known antibacterial agent is more effective at inhibiting bacterial growth than either agent alone and provide a rationale for coadministering such agents to patients suffering from bacterial infections.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed:

1. A method for treating a gram negative bacterial infection comprising coadministering to a patient in need of such treatment
   (a) a therapeutically effective amount of a DnaK inhibitor; and
   (b) a therapeutically effective amount of an antibacterial agent other than a DnaK inhibitor; wherein the treatment provides a synergistic antibacterial therapeutic effect with an overall response that is greater than the sum of the two individual antibacterial effects.

2. The method of claim 1, wherein the DnaK inhibitor is pyrrhocoricin, drosocin or an analog thereof.

3. The method of claim 2, wherein the antibacterial agent is a member of the fluoroquinolone, β-lactam, tetracycline, macrolide, aminoglycoside, glycopeptide, or folic acid synthesis inhibitor family of antibiotics.

4. The method of claim 3, wherein the DnaK inhibitor is an analog of pyrrhocoricin having the formula $R^1$-SEQ ID NO: 1-$R^2$,
   wherein SEQ ID NO: 1 is Asp-Lys-Gly-Ser-Tyr-Leu-Pro-Arg-Pro-Thr-Pro-Pro-Arg-Pro-Ile-Tyr-Asn-$R^3$ -,
   $R^1$ adds a net positive charge to the N-terminus of said peptide and is selected from the group consisting of
      (a) a positively charged reporter group;
      (b) a sequence of additional amino acids selected from the group consisting of Arg-Val, Lys-Val, Val and Lys-Val-Asp-Lys-Val (SEQ ID NO: 2), 1-amino-1-carboxycyclohexane and 4-amino-4-carboxypiperidine, wherein the N-terminal additional amino acid is optionally substituted by (a); and
      (c) an additional amino acid sequence Arg-Pro-Pro-Thr-Pro-Arg-Pro-Leu-Lys-Val (SEQ ID NO: 3) that cyclizes the peptide by bridging between the N- and C-termini thereof,
   $R^2$ selected from the group consisting of
      (a) a free hydroxyl, an amide, an imide, or a sugar; and
      (b) an additional amino acid selected from the group consisting of Asn, D-Asn, Asp, Asn substituted by a member selected from the group consisting of a free hydroxyl, an amide, an imide, and a sugar; and Asp substituted by a member selected from the group consisting of a free hydroxyl, an amide, an imide and a sugar; and
   $R^3$ is selected from the group consisting of arginine or α-N-alkylarginine, wherein alkyl represents a 1-6 carbon saturated chain.

5. The method of claim 4, wherein $R^2$ is the substituted Asn represented by Asn-$R^4$, $R^4$ is selected from the group consisting of (a) a free hydroxyl, an amide, an imide, or a sugar; and
      (b) a substituted amino acid represented by structural formula I

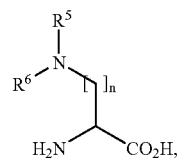

$R^5$ is selected from alkanoyl, aroyl or arylalkanoyl, $R^6$ is hydrogen or alkyl and n=1-4.

6. The method of claim 5, wherein $R^1$ is selected from the group consisting of valine, 1-amino-1-carboxycyclohexane, 4-amino-4-carboxypiperidine, $R^3$ is selected from the group consisting of arginine and N-alkylarginine, $R^4$ is a substituted amino acid represented by structural formula I

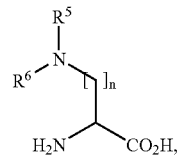

$R^5$ is selected from the group consisting of acetyl and $R^1$-SEQ ID NO: 1-$R^2$, $R^6$ is hydrogen and n=1 or 2.

7. The method of claim 1, wherein the DnaK inhibitor consists of:

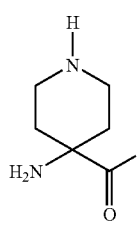
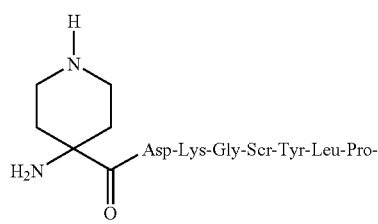
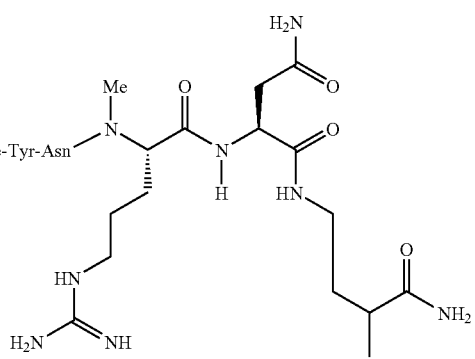
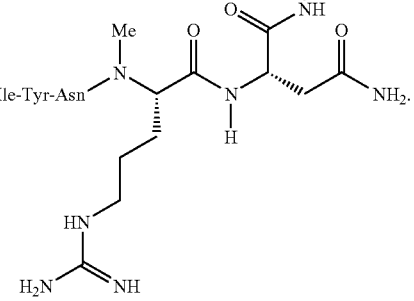

8. The method of claim 4 or 7, wherein the DnaK inhibitor and the antibacterial agent are administered substantially simultaneously.

9. The method of claim 4 or 7, wherein the DnaK inhibitor and the antibacterial agent are administered sequentially.

10. The method of claim 4 or 7, wherein the coadministration provides a synergistic antibacterial therapeutic effect with an overall response that is greater than the sum of the two individual antibacterial effects.

11. The method of claim 4 or 7, wherein the coadministration reduces the effective therapeutic dose of the antibacterial agent.

12. The method of claim 4 or 7, wherein the coadministration increases the spectrum of activity of the antibacterial agent.

13. The method of claim 4 or 7, wherein the coadministration reduces the incidence of resistance to the antibacterial agent.

14. The method of claim 4 or 7, wherein the coadministration extends the duration of activity of the antibacterial agent.

15. The method of claim 4, wherein $R^1$ is selected from the group consisting of 1-amino-1-carboxycyclohexane, 4-amino-4-carboxypiperidine and $R^2$ is a substituted amino acid.

16. The method of claim 15, wherein $R^1$ is 4-amino-4-carboxypiperidine, $R^2$ is a substituted amino acid having the structure $R^1$-SEQ ID NO: 1-$R^{2}$, wherein $R^1$ and $R^2$ are defined as above, and $R^3$ is α-N-alkylarginine.

17. The method of claim 16, wherein said antibacterial agent is a fluoroquinolone or an aminoglycoside.

18. The method of claim 17, wherein said fluoroquinolone is levofloxacin and said aminoglycoside is gentamycin.

* * * * *